US008664252B2

(12) United States Patent
Daemmgen et al.

(10) Patent No.: US 8,664,252 B2
(45) Date of Patent: Mar. 4, 2014

(54) PHOSPHODIESTERASE TYPE III (PDE III) INHIBITORS OR CA²⁺-SENSITIZING AGENTS FOR THE TREATMENT OF HYPERTROPHIC CARDIOMYOPATHY

(75) Inventors: Juergen Daemmgen, Ochsenhausen (DE); Olaf Joens, Ober-Hilbersheim (DE)

(73) Assignee: Boehringer Ingelheim Vetmedica GmbH, Ingelheim am Rhein (DE)

(*) Notice: Subject to any disclaimer, the term of this patent is extended or adjusted under 35 U.S.C. 154(b) by 0 days.

(21) Appl. No.: 13/126,541

(22) PCT Filed: Nov. 23, 2009

(86) PCT No.: PCT/EP2009/065618
§ 371 (c)(1),
(2), (4) Date: Jun. 8, 2011

(87) PCT Pub. No.: WO2010/060874
PCT Pub. Date: Jun. 3, 2010

(65) Prior Publication Data
US 2011/0251208 A1    Oct. 13, 2011

(30) Foreign Application Priority Data
Nov. 25, 2008 (EP) .................... 08169897

(51) Int. Cl.
*A01N 43/52* (2006.01)
*A61K 31/415* (2006.01)
*A01N 43/58* (2006.01)
*A61K 31/50* (2006.01)

(52) U.S. Cl.
USPC .......................... 514/395; 514/247

(58) Field of Classification Search
None
See application file for complete search history.

(56) References Cited

U.S. PATENT DOCUMENTS

| 4,361,563 | A | 11/1982 | Austel et al. |
| 4,596,705 | A | 6/1986 | Schepky et al. |
| 4,654,342 | A | 3/1987 | Slater |
| 4,868,182 | A | 9/1989 | Dage |
| 4,906,628 | A | 3/1990 | Coates |
| 4,954,501 | A | 9/1990 | Herter et al. |
| 5,024,998 | A | 6/1991 | Bodor |
| 5,151,420 | A | 9/1992 | Backstrom et al. |
| 5,364,646 | A | 11/1994 | Gruber et al. |
| 5,569,657 | A | 10/1996 | Nore et al. |
| 6,407,079 | B1 | 6/2002 | Muller et al. |
| 6,476,078 | B1 | 11/2002 | Jerussi et al. |
| 6,713,487 | B2 | 3/2004 | Yu et al. |
| 2003/0162835 | A1 | 8/2003 | Staniforth et al. |
| 2004/0037869 | A1 | 2/2004 | Cleverly et al. |
| 2005/0203097 | A1 | 9/2005 | Folger et al. |
| 2005/0239692 | A1 | 10/2005 | Lindenblatt et al. |
| 2007/0112010 | A1 | 5/2007 | Kleeman et al. |
| 2008/0207629 | A1 | 8/2008 | Folger et al. |
| 2009/0082282 | A1 | 3/2009 | Daemmgen et al. |
| 2010/0035889 | A1 | 2/2010 | Daemmgen et al. |
| 2010/0273807 | A1 | 10/2010 | Kleeman et al. |
| 2012/0148640 | A1 | 6/2012 | Folger et al. |
| 2013/0203690 | A1 | 8/2013 | Daemmgen et al. |

FOREIGN PATENT DOCUMENTS

| CA | 2034569 A1 | 7/1991 |
| CN | 1702243 A | 11/2005 |
| DE | 3728244 A1 | 3/1989 |
| EP | 0306846 A2 | 3/1989 |
| EP | 0330052 A2 | 8/1989 |
| EP | 0335545 A2 | 10/1989 |
| EP | 439030 A2 | 7/1991 |
| EP | 1579862 A1 | 9/2005 |
| JP | 2005281283 A | 10/2005 |
| WO | 8502767 A1 | 7/1985 |
| WO | 0197861 A2 | 12/2001 |
| WO | 03012030 A2 | 2/2003 |
| WO | 2004033444 A1 | 4/2004 |
| WO | 2004050657 A2 | 6/2004 |
| WO | 2004058726 A2 | 7/2004 |
| WO | 2005035505 A2 | 4/2005 |
| WO | 2005084647 A1 | 9/2005 |
| WO | 2005092343 A1 | 10/2005 |
| WO | 2005107756 A1 | 11/2005 |
| WO | WO 2005107756 A1 * | 11/2005 |
| WO | 2006022562 A1 | 3/2006 |
| WO | 2006060122 A2 | 6/2006 |
| WO | 2006060127 A2 | 6/2006 |
| WO | 2007054514 A2 | 5/2007 |
| WO | 2008055871 A1 | 5/2008 |

OTHER PUBLICATIONS van Meel et al., Journal of Cardiovascular Pharmacology 1989 (13) 508-509.*
Okazaki et al., Nature Genetics 1996 (13) 87-90.*
Choy et al., Journal of Applied Physiology 2007 (104) 1281-1286.*
Remme et al. Journal of Cardiovascular Pharmacology 1989 (14) S41-S44.*
Rodriguez et al., Compendium 2002 (24) 470-476.*
Roland et al., The 18th Annual ECVIM Congress 2008 abstract to a talk given between Sep. 4-6, 2008.*
Fujino et al. Pharmacology and Experimental Therapeutics 1988 (247) 519-523.*
Erhardt, L., "An Emerging Role for Calcium Sensitisation in the Treatment of Heart Failure". Expert Opinion on Investigational Drugs, vol. 14, No. 6, 2005, pp. 659-670.
Ng, TZien M.H., "Levosimendan, a New Calcium-Sensitizing Inotrope for Heart Failure". Pharmacotherapy, vol. 24, No. 10, 2004, pp. 1366-1384.
Written Opinion of the International Searching Authority for PCT/EP2009/065618 mailed Dec. 28, 2009.

(Continued)

*Primary Examiner* — Jeffrey S. Lundgren
*Assistant Examiner* — Michael Schmitt
(74) *Attorney, Agent, or Firm* — Michael P. Morris; Wendy M. Gombert

(57) ABSTRACT

The present invention relates to a phosphodiesterase type III (PDE III) inhibitor and/or Ca²⁺-sensitizing agent or a pharmaceutically acceptable derivative thereof for the treatment of a patient suffering from hypertrophic cardiomyopathy (HCM). According to another aspect the present invention relates to the use of a PDE III inhibitor and/or Ca²⁺-sensitizing agent for the preparation of a medicament for the treatment of a patient suffering from HCM.

15 Claims, No Drawings

(56) References Cited

OTHER PUBLICATIONS

Groban, Leanne, "Diastolic Dysfunction in the Older Heart". Journal of Cardiothoracic and Vascular Anesthesia, vol. 19, No. 2, Apr. 2005, pp. 228-236.
International Search Report for PCT/EP2009/065618 mailed Dec. 28, 2009.
Mamoru et al., "Effects of Long-term, Very-low-dose Pimobendan for Patients with Diastolic Heart Failure". Journal of Cardial Failure, vol. 12, No. 8, Oct. 2006, p. S171.
Abstract in English for DE3728244,1989.
Abstract in English for EP0306846, 1989.
Abstract in English for EP0330052, 1989.
Borgarelli et al., "Canine Idiopathic Dilated Cardiomyopathy. Part II: Pathophysiology and therapy". The Veterinary Journal, vol. 162, 2001, pp. 182-195.
Calvert et al., "Congestive cardiomyopathy in Doberman Pinscher dogs". Journal of the American Veterinary Medical Association, vol. 181, 1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Chetboul, et al., "Comparitive Adverse Cardiac Effects of Pimobendan and Benazepril Monotherapy in Dogs with Mild Degenerative Mitral Valve Disease: A Prospective, Controlled, Blinded, and Randomized Study". Journal of Veterinary Internal Medicine, vol. 21, 2007, pp. 742-753.
Cohn et al., "Cardiac Remodeling-Concepts and Clinical Implications: A Consensus Paper From an International Forum on Cardiac Remodeling". Journal of the American College of Cardiology, vol. 35, No. 3, 2000, pp. 569-582.
Cowley et al, "Treatment of severe heart failure: quantity or quality of life? A trial of enoximone"., British Heart Journal, vol. 72, 1994, pp. 226-230.
Elliott, P., "Diagnosis and management of dilated cardiomyopathy". Heart, vol. 83, 2000, pp. 106-112.
Ettinger et al., "Effects of enalapril maleate on survival of dogs with naturally acquired heart failure". Journal of the American Veterinary Medical Association, vol. 213, No. 11, 1998, pp. 1573-1577.
Fitton et al., "Pimobendan. A Review of its Pharmacology and Therapeutic Potential in Congestive Heart Failure". Drugs and Aging, vol. 4, No. 5, 1994, pp. 417-441.
Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.
Häggström et al., "New insights into degenerative mitral valve disease in dogs". Veterinary Clinics Small Animal Practice, vol. 34, 2004, pp. 1209-1226.
Katz et al., "A multicenter, randomized, double-blind, placebo-controlled trial of pimobendan, a new cardiotonic and vasodilator agent, in patients with severe congestive heart failure". American Heart Journal, vol. 123, 1992, pp. 95-103.
Kubo et al, "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.
Kvart et al., "Efficacy of Enalapril for Prevention of Congestive Heart Failure in Dogs with Myxomatous Valve Disease and Asymptomatic Mitral Regurgitation". Journal of Veterinary Internal Medicine, vol. 16, 2002, pp. 80-88.
Lip et al., "ABC of heart failure: Aetiology". British Medical Journal, vol. 320, Jan. 2000, pp. 104-107.
McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp. 54-59. Originally published online Jun. 23, 2003, http://circ.ahajournals.org, 7 pages.
Monnet et al., "Idiopathic Dilated Cardiomyopathy in Dogs: Survival and Prognostic Indicators". 1995, Journal of Veterinary Internal Medicine, vol. 9, No. 1, pp. 12-17.
O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.
Packer et al., "Effect Of Oral Milrinone On Mortality In Severe Chronic Heart Failure." The New England Journal of Medicine, vol. 325, No. 21, Nov. 1991, pp. 1468-1475.
Piel et al., "Development of a parenteral and of an oral formulation of albendazole with cyclodextrins". S.T.P. Pharma Sciences, vol. 9, No. 3, 1999, pp. 257-260.
Remme et al., "Hemodynamic, Neurohumoral, and Myocardial Energetic Effects of Pimobendan, a Novel Calcium-Sensitizing Compound, in Patients with Mild to Moderate Heart Failure". Journal of Cardiovascular Pharmacology, vol. 24, No. 5, 1994, pp. 730-739.
Sisson, David, "Lecture Notes: Cardiology", The District of Columbia Academy of Veterinary Medicine, May 2001, pp. 1-18.
Woolley et al., "Effects of Treatment Type on Vertebral Heart Size in Dogs With Myxomatous Mitral Valve Disease". The Journal of Applied Research in Veterinary Medicine, vol. 5, No. 1, 2007, pp. 43-48.
Abstract in English for CN1702243A, 2005.
Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.
Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.
Côté et al., "Congestive Heart Failure". Feline Cardiology, Ch. 19, Wiley-Blackwell, ISBN 978-0-8138-1242-7, 2011, p. 259.
Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.
Fox, Philip R., "Hypertrophic Cardiomyopathy. Clinical and Pathologic Correlates". Journal of Veterinary Cardiology, vol. 5, No. 2, Nov. 2003, pp. 39-45.
Abstract in English for JP2005281283, 2005.
Endoh, Masao, "New Aspects of the Treatment of Myocardial Failure from a Pharmacological Standpoint". Journal of Clinical and Experimental Medicine, vol. 187, No. 10, 1998, pp. 827-831.
Häggström et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.
Sabbah et al., "Effects of long-term monotherapy with enalapril, metoprolol, and digoxin on the progression of left ventricular dysfunction and dilation in dogs with reduced ejection fraction". Circulation, vol. 89, 1994, pp. 2852-2859.
Kittleson et al., "The Acute Hemodynamic Effects of Milrinone in Dogs With Severe Idiopathic Myocardial Failure". Journal of Veterinary Medicine, vol. 1, 1987, pp121-127.

* cited by examiner

PHOSPHODIESTERASE TYPE III (PDE III) INHIBITORS OR CA$^{2+}$-SENSITIZING AGENTS FOR THE TREATMENT OF HYPERTROPHIC CARDIOMYOPATHY

FIELD OF THE INVENTION

The invention relates to the field of medicine, in particular to the field of veterinary medicine. The invention relates to phosphodiesterase type III (PDE III) inhibitors, Ca$^{2+}$-sensitizing agents or a pharmaceutically acceptable derivative thereof for the treatment of diastolic dysfunction, preferably related to hypertrophic cardiomyopathy (HCM) in a patient.

BACKGROUND OF THE INVENTION

Hypertrophic cardiomyopathy (HCM) is the most common heart disease in cats and the most common cause of heart failure in this species (Riesen et al., 2007; Rush et al., 1998). While a genetic mutation of one or more of the sarcomeric proteins has been proposed to be the cause of HCM in most cats, a specific mutation has only been identified for Maine coon and Ragdoll cats (Meurs et al., 2005 and 2007; Kittleson et al., 1999). In most cats identified to have HCM, the heart disease is the eventual cause for death. HCM together with restrictive cardiomyopathy (RCM) are classified as diasystolic dysfunctions.

Five common phenotypical manifestations of feline HCM include 1) diffuse, symmetric concentric hypertrophy of the left ventricle (LV); 2) asymmetric hypertrophy of the interventricular septum (IVS) with a normal LV free wall, such that the IVS impinges into the left ventricular outflow tract during systole; 3) asymmetric hypertrophy of the left ventricular free wall (with normal thickness of the IVS); 4) midventricular hypertrophy of the left ventricle with sparing of the cardiac base and the apex causing mid-ventricular obstruction; and 5) isolated papillary muscle hypertrophy most often seen in Maine Coon cats (Peterson et al., 1993; Fox 2003; Liu et al., 1993; Kittleson et al., 1999).

Treatment of symptoms of HCM is directed towards decreasing the left ventricular outflow tract gradient and symptoms of dyspnea, chest pain and syncope. Medical therapy is successful in the majority of patients. The first medication that is routinely used is a β-blocker (metopolol, atenolol, bisoprolol, propranolol). If symptoms and gradient persist, disopyramide may be added to the β-blockers. Alternately a calcium channel blocker such as verapamil may be substituted for a beta blocker.

Restrictive cardiomyopathy (RCM) is a form of cardiomyopathy in which the walls are rigid, and the heart is restricted from stretching and filling with blood properly. Rhythmicity and contractility of the heart may be normal, but the stiff walls of the heart chambers (atria and ventricles) keep them from adequately filling, reducing preload and end-diastolic volume. So blood flow is reduced, and blood that would normally enter the heart is backed up in the circulatory system. In time, restrictive cardiomyopathy patients develop diastolic dysfunction and eventually heart failure.

PDE III Inhibitors and Ca$^{2+}$-sensitizing agents such a pimobendan or levosimendan are well-known compounds for the treatment of heart failure (HF) originating from dilated cardiomyopathy (DCM) or decompensated endocardiosis (DCE) in animals, especially for the treatment of dogs suffering from heart failure (see for example WO 2005/092343). PDE-III inhibitors including those having Ca$^{2+}$-sensitizing effects and Ca$^{2+}$-sensitizing agents are known to be inotropic and may increase the contractility of the left ventricle. Therefore, it was believed that use of PDE III inhibitors including those having Ca$^{2+}$-sensitizing effects and Ca$^{2+}$-sensitizing agents are contraindicated for the treatment of HCM.

Concentric hypertrophy of the left ventricle results in a reduced left ventricular internal dimension and slowed ventricular relaxation, and consequently impedes diastolic filling. Altered diastolic filling and compromised myocardial blood flow result in myocardial ischemia and, as a consequence of ischemia, a progressive loss of cardiomyocytes. Over time, the heart becomes stiff and non-compliant and the hypertrophied muscle is replaced with fibrous tissue which further impedes diastolic filling. PDE-III Inhibitors by inhibiting the breakdown of the second messenger of catecholamines (increase in cytosolic cAMP and Ca$^{2+}$ due to inhibition of PDE-III) and increasing the sensitivity of the contractile proteins towards Ca$^{2+}$ would be expected to further impair diastolic ventricular function, when administered to those patients. Moreover, enhancing systolic function would lead to further increase of the left ventricular (LV) wall, especially in those segments, where the pathoanatomical changes have resulted in obstruction of the left ventricular outflow and would thus further deteriorate left ventricular pump function. Evidence for the latter hypothesis is given by clinical observations that can be made especially under the influence of stress, which is frequently induced by clinical examination of cats: As the cat becomes excited, the murmur increases in intensity as a result of increased heart rate, increased systolic inotropic state, and increased velocity of blood flow in the LV outflow tract, and the resulting mitral regurgitation. The LV outflow tract obstruction, due either to systolic bulging of the bicuspid valve or hypertrophy at the top of the interventricular septum, may lead to increased systolic wall stress, increased myocardial oxygen demand with demand-supply mismatch, worsening of LV hypertrophy, acceleration of diastolic dysfunction, arrhythmias, and finally disease progression over time. This is one of the reasons that many clinicians prescribe bradycardic agents to keep the heart rate slow and blunt this dynamic worsening of the left ventricular outflow tract obstruction. Moreover, Tilley and co-workers demonstrated the deleterious rise in left ventricular end diastolic pressures which results from sympathetic stimulation in 19 cats with HCM (Tilley et al., 1977). This sudden rise in LV end diastolic pressure results in elevated left atrial pressure and subsequent acute pulmonary edema. This model, which used isoproterenol infusion, is thought to mimic the rise in sympathetic tone associated with stressful events in cats which can lead to an abrupt onset of pulmonary edema in a previously well-compensated animal.

The problem underlying the present invention was to provide a medication, which allows the treatment of diastolic dysfunction, preferably HCM and to reduce the risk of death in patients with heart failure associated with diastolic dysfunction, in particular with HCM. In particular, the problem underlying the present invention was to provide a medication which allows the treatment of HCM in patients suffering from heart failure.

BRIEF DESCRIPTION OF THE INVENTION

Contrary to the general doctrine not to use inotropic agents such as PDE III inhibitors and Ca$^{2+}$-sensitizing agents for the treatment of HCM, it has surprisingly been found that PDE III inhibitors and/or Ca$^{2+}$-sensitizing agents can be used for the treatment of patients suffering from HCM. More in general, inotropic and vasodilator agents such as PDE III inhibitors and Ca$^{2+}$-sensitizing agents can be used for the treatment of diastolic dysfunctions, in particular HCM and/or RCM. Thus, according to one aspect the present invention relates to PDE III inhibitors and/or $Ca^{2+}$-sensitizing agents for the treatment of HCM, respectively for the treatment of a patient suffering from HCM. According to a further aspect, the present invention relates to PDE III inhibitors and/or $Ca^{2+}$-sensitizing agents for the treatment of diastolic dysfunction, preferably in form of HCM and/or RCM, respectively for the treatment of a patient suffering from diastolic dysfunction, preferably suffering from HCM and/or RCM.

According to a further aspect the present invention relates to use of PDE III inhibitors and/or $Ca^{2+}$-sensitizing agents for the preparation of a medicament/pharmaceutical composition for the treatment of diastolic dysfunction, preferably HCM and/or RCM, respectively for the treatment of a patient suffering from diastolic dysfunction, preferably HCM and/or RCM.

Preferably, the PDE III inhibitor and the $Ca^{2+}$-sensitizing agent, respectively, are selected from the group consisting of cilostazol, pimobendan, milrinone, levosimendan, amrinone, enoximone and piroximone TZC-5665, pharmaceutically acceptable salts thereof, derivatives thereof, metabolites thereof and any pro-drugs thereof.

DESCRIPTION OF THE INVENTION

Detailed Description of the Invention

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

The invention relates to PDE III inhibitors and/or $Ca^{2+}$-sensitizing agents, preferably a PDE III inhibitor which exhibits additionally calcium sensitising effect such as pimobendan for the treatment of diastolic dysfunction, preferably of HCM and/or RCM, most preferably of HCM, in particular for the treatment of a patient suffering from diastolic dysfunction, preferably of HCM and/or RCM, most preferably of HCM. The present invention not only relates to the specific use of PDE III inhibitors and/or $Ca^{2+}$-sensitizing agents, preferably a PDE III inhibitor which exhibits additionally calcium sensitising effect such as pimobendan for the treatment of HCM, it also relates to the use PDE III inhibitors and/or $Ca^{2+}$-sensitizing agents, preferably, PDE III inhibitor which exhibits additionally calcium sensitising effect such as pimobendan for the preparation of a medicament/pharmaceutical composition for the treatment of a patient suffering from diastolic dysfunction, preferably from HCM and/or RCM, most preferably from HCM.

Heart failure caused by diastolic dysfunction is generally described as the failure of the ventricle to adequately relax and typically denotes a stiffer ventricular wall. This causes inadequate filling of the ventricle, and therefore results in an inadequate stroke volume. The failure of ventricular relaxation also results in elevated end-diastolic pressures, and the end result is identical to the case of systolic dysfunction (pulmonary edema in left heart failure, peripheral edema in right heart failure.) Diastolic dysfunction can be caused by processes similar to those that cause systolic dysfunction, particularly causes that affect cardiac remodeling. Diastolic dysfunction may not manifest itself except in physiologic extremes if systolic function is preserved. At least to forms of diastolic dysfunction are known (HCM or RCM).

HCM normally is associated with or caused acute or chronic heart failure (heart failure). Therefore, the present invention also relates to PDE III inhibitors and/or $Ca^{2+}$-sensitizing agents, preferably a PDE III inhibitor which exhibits additionally calcium sensitising effect such as pimobendan for the treatment of HCM in patients suffering from heart failure.

HCM can be defined as obstructive or non-obstructive. The obstructive variant of HCM, hypertrophic obstructive cardiomyopathy (HOCM) has also historically been known as idiopathic hypertrophic subaortic stenosis (IHSS) and asymmetric septal hypertrophy (ASH). A non-obstructive variant of HCM is apical hypertrophic cardiomyopathy.

Thus, according to a further aspect the present invention relates to PDE III inhibitors and/or $Ca^{2+}$-sensitizing agents, preferably a PDE III inhibitor which exhibits additionally calcium sensitising effect such as pimobendan for the treatment of HCM, in particular for the treatment of a patient suffering from obstructive or non-obstructive HCM. Moreover, the present invention also relates to the use of PDE III inhibitors and/or $Ca^{2+}$-sensitizing agents, preferably a PDE III inhibitor which exhibits additionally calcium sensitising effect such as pimobendan for the preparation of a medicament/pharmaceutical composition for the treatment of a patient suffering from obstructive or non-obstructive HCM.

According to a further aspect the present invention relates to PDE III inhibitors and/or $Ca^{2+}$-sensitizing agents, preferably a PDE III inhibitor which exhibits additionally calcium sensitising effect such as pimobendan for the treatment of HCM, in particular for the treatment of a patient suffering from obstructive HCM, preferably from hypertrophic obstructive cardiomyopathy (HOCM) or and asymmetric septal hypertrophy (ASH).

According to a further aspect the present invention relates to PDE III inhibitors and/or $Ca^{2+}$-sensitizing agents, preferably a PDE III inhibitor which exhibits additionally calcium sensitising effect such as pimobendan for the treatment of HCM, in particular for the treatment of a patient suffering from non-obstructive HCM, preferably from apical hypertrophic cardiomyopathy.

The term "PDE III inhibitor" as used herein relates to phosphodiesterase (PDE) III inhibitors including pharmaceutically acceptable derivative thereof, which prevent breakdown of cAMP to 5'AMP and thus maintain the effect of cAMP on protein kinase and other secondary messenger activation.

The "term $Ca^{2+}$-sensitizing agent" relates to any compound including pharmaceutically acceptable derivatives thereof which increases the $Ca^{2+}$ sensitivity of cardiac contractile proteins, i.e. increase the developed contractile force at a given concentration of $Ca^{2+}$.

PDE III inhibitors and $Ca^{2+}$-sensitizing agent are well known in the art and described for instance in U.S. Pat. No. 4,906,628; U.S. Pat. No. 4,654,342; U.S. Pat. No. 4,361,563; U.S. Pat. No. 5,569,657; U.S. Pat. No. 5,151,420; or EP B-008 391.

Preferred PDE III inhibitors and/or $Ca^{2+}$-sensitizing agents are cilostazol, pimobendan, milrinone, levosimendan, amrinone, enoximone and piroximone TZC-5665 or pharmaceutically acceptable salts, derivatives, metabolites or pro-drugs thereof. Most preferred PDE III inhibitors and $Ca^{2+}$-sensitizing agents, respectively are pimobendan and levosimendan, or pharmaceutically acceptable salts, derivatives, metabolites or pro-drugs thereof. Most preferred is pimobendan, pharmaceutically acceptable salts, derivatives, metabolites or pro-drugs thereof.

Pimobendan (4,5-dihydro-6-[2-(4-methoxyphenyl)-1H-benzimidazol-5-yl]-5-methyl-3 (2H)-pyridazinone) is disclosed in EP B-008 391, herein incorporated by reference in its entirety. Pimobendan having the formula:

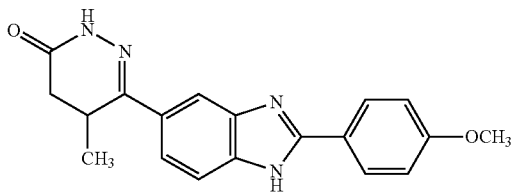 [SMILES: COc1ccc(-c2nc3cc(C4=NNC(=O)CC4C)ccc3[nH]2)cc1]

Pimobendan is a well-known compound for the treatment of heart failure (HF) originating from dilated cardiomyopathy (DCM) or decompensated endocardiosis (DCE) in animals, in particular in dogs (WO 2005/092343). Pimobendan is also approved as a drug product for cardiovascular treatment of humans.

Levosimendan is a pyridazone-dinitrile derivative. In particular, levosimendan is known to the public as (R)-[[4-(1,4,5,6-Tetrahydro-4-methyl-6-oxo-3-pyridazinyl)phenyl]hydrazono]propanedinitrile and has been described earlier for example in GB 2228004, U.S. Pat. No. 5,151,420 and U.S. Pat. No. 5,569,657, herein incorporated by reference in its entirety. Levosimendan having the formula:

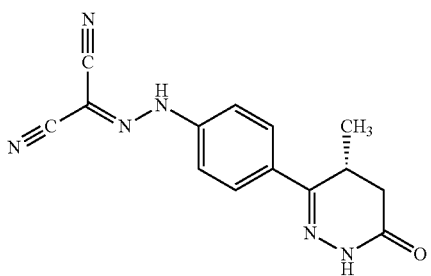 [SMILES: C[C@@H]1CC(=O)NN=C1c1ccc(NN=C(C#N)C#N)cc1]

The term "patient" as used herein relates but is not limited to an animal or a person suffering from diastolic dysfunction, preferably from HCM and/or RCM, most preferably from HCM. The term "patient" embraces mammal such as primates including humans.

In addition to primates, a variety of other mammals can be treated according to the method of the present invention. For instance, mammals including but not limited to cows, sheep, goats, horses, dogs, cats, guinea pigs, rats or other bovine, ovine, equine, canine, feline, rodent or murine species can be treated. However, the method can also be practiced in other species, such as avian species.

Preferred are human patients, dogs, cats and horses. Most preferred are cats. Human patients are female or male person who are suffering from heart failure. As a rule such persons are children, young adults, adults or elderly people with an age of between 6 and 80, preferably between 30 and 65 years.

The term "heart failure" as used herein relates to condition in which a problem with the structure or function of the heart impairs its ability to supply sufficient blood flow to meet the body's needs, in particular any contractile disorder or disease of the heart. Clinical manifestations are as a rule the results of changes to the heart's cellular and molecular components and to mediators that drive homeostatic control. Heart failure is caused by several clinical apparent disorders including myocardial infarction and other forms of ischemic heart disease, hypertension, valvular heart disease and cardiomyopathy such as hypertrophic cardiomyopathy.

The term "effective amount" as used herein means an amount sufficient to achieve a reduction of hypertrophic cardiomyopathy in a patient when a PDE III inhibitor and/or $Ca^{2+}$-sensitizing agent is administered at a dosage as described herein. The progress of the therapy (reduction diastolic dysfunction, preferably of HCM and/or RCM, most preferably of HCM as described herein) can be monitored by standard cardiologic diagnosis, for example, by echocardiography, cardiac catheterization, or cardiac MRI, or cardiac magnetic resonance imaging.

The term "pharmaceutically acceptable derivative thereof" means but is not limited to pharmaceutically acceptable salts, derivatives, metabolites or pro-drugs of a drug. Derivatives as used herein include but are not limited to, any hydrate forms, solvates, isomers, enantiomers, racemates, racemic conglomerate and the like of the compound of choice. Suitable pharmaceutically acceptable salts are well known in the art and may be formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

Dosage

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

A physician or veterinarian can determine and prescribe the effective amount of the drug required to prevent, counter, or arrest the progress of the disorder. By way of general guidance, the daily dosage of each active ingredient, preferably of pimobendan or levosimendan, when used for the indicated effects, will range between 5 and 2.500 μg/kg bodyweight, preferably 10 to 1,500 μg/kg bodyweight, even more preferred between 15 to 750 μg/kg bodyweight, even more preferred between 15 and 500 μg/kg bodyweight, most preferred between 20 and 250 µg/kg bodyweight. Those dosages should be administered once per day or split into twice daily administration. The treatment is advisable in clinically apparent cases, both in acute as well as in chronic settings.

Thus according to further aspect the present invention relates to a PDE III inhibitor and/or $Ca^{2+}$-sensitizing agent, preferably a PDE III inhibitor which exhibits additionally calcium sensitising effect such as pimobendan for the preparation of a medicament/pharmaceutical composition for the treatment of a patient suffering from diastolic dysfunction, preferably of HCM and/or RCM, most preferably of acute or chronic HCM.

Preferably the PDE III inhibitor and/or $Ca^{2+}$-sensitizing agent, preferably a PDE III inhibitor which exhibits additionally calcium sensitising effect such as pimobendan is used for the treatment of a patient suffering from diastolic dysfunction, preferably from HCM and/or RCM, most preferably from HCM, wherein the dosage to be administered is in the range between 5 and 2,500 µg/kg bodyweight per day, preferably in the range between 10 to 1,500 µg/kg bodyweight per day, even more preferred in the range between 15 to 750 µg/kg bodyweight per day, even more preferred in the range between 15 and 500 µg/kg bodyweight per day, most preferred in the range between 20 and 250 µg/kg bodyweight per day.

The pharmaceutical composition comprising the PDE-III inhibitor and/or $Ca^{2+}$-sensitizing agent, preferably the PDE III inhibitor which exhibits additionally calcium sensitising effect such as pimobendan for the treatment of diastolic dysfunction, preferably of HCM and/or RCM, most preferably of HCM is prepared to be used in a dosage range between 5 and 2,500 µg/kg bodyweight per day, preferably in a dosage range between 10 to 1,500 µg/kg bodyweight per day, even more preferred in a dosage range between 15 to 750 µg/kg bodyweight per day, even more preferred in a dosage range between 15 and 500 µg/kg bodyweight per day, most preferred in a dosage range between 20 and 250 µg/kg bodyweight per day.

Administration

The compounds of this invention can be administered in an oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

Combined Use

Preferably, the PDE III inhibitor and/or $Ca^{2+}$-sensitizing agent, preferably the PDE III inhibitor which exhibits additionally calcium sensitising effect such as pimobendan are administered in combination with a second active therapeutic agent. Preferably, such second active therapeutic agent is furosemide. Furosemide should be dosed at 0.5 to 5 mg/kg once or twice daily. It may well be that furosemide can be completely withdrawn once the patient has been stabilized.

Thus, according to a further aspect the present invention relates to the combined use of a PDE III inhibitor and/or $Ca^{2+}$-sensitizing agent, preferably a PDE III inhibitor which exhibits additionally calcium sensitising effect such as pimobendan pimobendan with furosemide for the treatment of a patient suffering from diastolic dysfunction, preferably from HCM and/or RCM, most preferably from HCM. Preferably, the PDE III inhibitor and/or $Ca^{2+}$-sensitizing agent, preferably the PDE III inhibitor which exhibits additionally calcium sensitising effect such as pimobendan and the furosemide are administered at the dosages described herein.

According to a further aspect the present invention relates to a two phase combination therapy for the treatment of a patient suffering from diastolic dysfunction, preferably from HCM and/or RCM, most preferably from HCM, comprising in the first phase the administration of a PDE III inhibitor and/or $Ca^{2+}$-sensitizing agent, preferably a PDE III inhibitor which exhibits additionally calcium sensitising effect such as pimobendan in combination with furosemide, and in the second phase the administration of the PDE III inhibitor and/or $Ca^{2+}$-sensitizing agent, preferably the PDE III inhibitor which exhibits additionally calcium sensitising effect such as pimobendan without using furosemide. Preferably, the PDE III inhibitor and/or $Ca^{2+}$-sensitizing agent, preferably the PDE III inhibitor which exhibits additionally calcium sensitising effect such as pimobendan and the furosemide are administered at the dosages described herein.

From the pathophysiology of the disease one would expect that further improvement of diastolic function by prolongation of diastole or enhancing coronary perfusion/oxygen supply-demand ratio should be key targets of pharmacotherapy. Both effects could be achieved by reducing cardiac rate. Reduction of heart rate could be induced by certain blockers of the L-type calcium channels, by β-adrenoreceptor antagonists or by blockers of the hyperpolarisation-dependent inward current of sinoatrial pacemaker cells. It can be expected that PDE-III inhibitors or $Ca^{2+}$-sensitizing agents, preferably pimobendan combines favourably with those agents, especially with β-blockers or if-blockers as PDE III inhibitor and/or $Ca^{2+}$-sensitizing agent, preferably a PDE III inhibitor which exhibits additionally calcium sensitising effect such as pimobendan may counteract direct or indirect, i.e. rate related impairment of cardiac contractile force inherent to those agents as well as concurrent vasoconstriction.

Moreover, unburdening of the heart by peripheral vasodilation as well as improving coronary perfusion, due to direct coronary vasodilation or the reduction of extramural resistance following the diminution of cardiac preload as induced by PDE III inhibitors, will further contribute to the improvement of diastolic wall function.

Thus, according to a further aspect the present invention relates to the combined use of a PDE III inhibitor and/or $Ca^{2+}$-sensitizing agent, preferably a PDE III inhibitor which exhibits additionally calcium sensitising effect such as pimobendan with a L-type calcium channel blocker, a β-adrenoreceptor antagonists, and/or a if-blocker for the treatment of a patient suffering from diastolic dysfunction, preferably from HCM and/or RCM, most preferably from HCM.

Well known "L-type calcium channel blockers" include, but are not limited to diltiazem, verapamil and felodipine or pharmaceutically acceptable derivative thereof.

Well known "β-adrenoreceptor antagonists" include, but are not limited to atenolol and carvedilol, propranolol, metoprolol, sotalol, timolol, bupranolol, esmolol, nebivolol, bisoprolol. Preferred β-adrenoreceptor antagonists are carvedilol, sustaine-release metoprolol anf nebivolol.

Well known "if-blockers" include, but are not limited to cilobradine or ivabradine.

The L-type calcium channel blocker, a β-adrenoreceptor antagonists, and/or a if-blockers as listed above also include any pharmaceutical acceptable derivative thereof. For instance the term diltiazem shall also mean and include any pharmaceutical acceptable derivatives of diltiazem.

According to a further aspect the PDE III inhibitor and/or $Ca^{2+}$-sensitizing agent, preferably the PDE III inhibitor which exhibits additionally calcium sensitising effect such as pimobendan can be used in combination with an ACE inhibitor for the treatment of a patient suffering from diastolic dysfunction, preferably from HCM and/or RCM, most preferably from HCM.

Well known "ACE inhibitors" include, but are not limited to omapatrilat, MDL100240, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril or a pharmaceutically acceptable derivative thereof.

Thus, according to a further aspect the present invention relates to the combined use of a PDE III inhibitor and/or $Ca^{2+}$-sensitizing agent, preferably a PDE III inhibitor which exhibits additionally calcium sensitising effect such as pimobendan with ACE inhibitor for the treatment of a patient suffering from diastolic dysfunction, preferably from HCM and/or RCM, most preferably from HCM, wherein the ACE inhibitor is selected from the group consisting of omapatrilat, MDL100240, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril or a pharmaceutically acceptable derivative thereof.

EXAMPLES

The following examples serve to further illustrate the present invention; but the same should not be construed as a limitation of the scope of the invention disclosed herein.

Example 1

Treatment of Cats Suffering from HCM

A 15 year old castrated male tomcat of mixed breed (mother Persian, father European short hair, bodyweight 6 kg) was brought to the veterinary clinic in March 2008. The animal was lethargic and unable to move. Examination of the cardiovascular system indicated acute circulatory failure, accompanied with tachycardia (>180 bpm). Echocardiographic investigation indicated a thickened left ventricular wall and septum, which are related to HCM.

Immediate administration of furosemide, 1 mg/kg i.v. did not result in a sufficient control of the situation. Because of the desperate situation 1.25 mg pimobendan were applied orally with the expectation/fear that this measure would/could probably further deteriorate the status of the cat.

Very much to the surprise, the clinical symptoms improved and the cat recovered within a few hours. As the owner had observed that the cat had been unusually inactive before the acute crisis and as the cat tended to deteriorate on the following day the veterinarian decided to continue the treatment at a dose of 20 microgram/kg/day pimobendan orally. This treatment is still being continued. Yet, the data obtained via ultrasound proved a significant recovery of left ventricular filling and systolic function.

REFERENCES

Fox P R. Hypertrophic cardiomyopathy. Clinical and pathologic correlates. *J Vet Cardiol* 2003; 5:39-45.
Kittleson M D, Meurs K M, Munro M J, et al. Familial hypertrophic cardiomyopathy in Maine coon cats. *Circulation* 1999; 99:3172-3180.
Liu S K, Roberts W C, Maron B J. Comparison of morphologic findings in spontaneously occurring hypertrophic cardiomyopathy in humans, cats, and dogs. *Am J Cardiol* 1993; 72:944-951.
Meurs K M, Sanchez X, David R M, et al. A cardiac myosin binding protein C mutation in the Main coon cat with familial hypertrophic cardiomyopathy. *Human Molecular Genetics* 2005: 14:3587-3593.
Meurs K M, Norgard M M, Ederer M M, et al. A substitution mutation in the myosin binding protein C gene in ragdoll hypertrophic cardiomyopathy. Genomics 2007; 90:261.
Peterson E N, Mooise N S, Brown C A, et al. Heterogeneity of hypertrophy in feline hypertrophic heart disease. *JVIM* 1993; 7:183-189
Riesen S C, Kovacevic A, Lombard C W, et al. Prevalence of heart disease in symptomatic cats: an overview from 1998 to 2005. *Schweizer Archiv fur Tierheilkunde* 2007; 149:65-71.
Rush J E. Therapy of feline hypertrophic cardiomyopathy. *Veterinary Clinics of North America: Small Animal Practice* November 1998; 28:1459-1479
Tilley L P, Weitz J. Pharmacologic and other forms of medical therapy in feline cardiac disease. *Veterinary Clinics of North America* May 1977; 7:415-420.

The invention claimed is:

1. A method of treating a feline suffering from hypertrophic cardiomyopathy, the method comprising administering a medicament comprising an effective amount of pimobendan to a feline suffering from hypertrophic cardiomyopathy, the effective amount of pimobendan being a daily dosage of from 10 µg/kg feline bodyweight to 1500 µg/kg feline bodyweight.

2. The method of claim 1, wherein said administering the medicament comprises oral administration of the medicament.

3. The method of claim 1, wherein said administering the medicament comprises parenteral administration of the medicament.

4. The method of claim 1, wherein said daily dosage is between 20 to 250 micrograms of pimobendan per kilogram of the feline's bodyweight.

5. The method of claim 1, wherein said administering the medicament further comprises administering the medicament together with furosemide.

6. The method of claim 5, wherein the furosemide is administered in a dosage between 0.5 to 5 milligrams of furosemide per kilogram of the feline's bodyweight once or twice daily.

7. The method of claim 5, wherein the furosemide is administered parenterally.

8. The method of treating a feline according to claim 1, wherein the medicament is administered once in a 24 hour period.

9. The method of treating a feline according to claim 1, wherein the daily dosage is administered in two doses within a 24 hour period.

10. The method of treating a feline according to claim 1, wherein the method comprises a two phase combination therapy including:

administering daily a first medicament comprising the effective amount of pimobendan in combination with an effective amount of furosemide for a first predetermined period of time; and administering daily a second medicament comprising the effective amount of pimobendan and no furosemide for a second predetermined period of time.

11. The method of treating a feline according to claim 1, wherein the medicament further comprises an ingredient selected from the group consisting of an L-type calcium channel blocker; a β-adrenoreceptor antagonist; and an if-blocker.

12. The method of treating a feline according to claim 1, wherein the medicament further comprises an angiotensin-converting enzyme (ACE) inhibitor.

13. The method of treating a feline according to claim 1, wherein the ACE inhibitor is selected from the group consisting of omapatrilat, MDL100240, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat, and spirapril.

14. The method of treating a feline according to claim 1, wherein the treatment is effective to increase the $Ca^{2+}$ sensitivity of cardiac contractile proteins by increasing the developed contractile force at a predetermined concentration of $Ca^{2+}$.

15. The method of treating a feline according to claim 1, wherein administration of the effective amount achieves a reduction of the hypertrophic cardiomyopathy.

\* \* \* \* \*